(12) United States Patent
Beck

(10) Patent No.: US 9,223,001 B2
(45) Date of Patent: Dec. 29, 2015

(54) MR IMAGING USING NAVIGATORS

(75) Inventor: Gabriele Marianne Beck, Venlo (NL)

(73) Assignee: Koninklijke Philips N.V., Eindhoven (NL)

( * ) Notice: Subject to any disclaimer, the term of this patent is extended or adjusted under 35 U.S.C. 154(b) by 768 days.

(21) Appl. No.: 13/505,296

(22) PCT Filed: Oct. 26, 2010

(86) PCT No.: PCT/IB2010/054842
§ 371 (c)(1),
(2), (4) Date: Jun. 4, 2012

(87) PCT Pub. No.: WO2011/055268
PCT Pub. Date: May 12, 2011

(65) Prior Publication Data
US 2013/0127460 A1  May 23, 2013

(30) Foreign Application Priority Data

Nov. 5, 2009 (EP) .................................... 09175131

(51) Int. Cl.
*G01R 33/565* (2006.01)
*G01N 24/08* (2006.01)
(Continued)

(52) U.S. Cl.
CPC .......... *G01R 33/56572* (2013.01); *G01N 24/08* (2013.01); *G01R 33/5676* (2013.01); *G01R 33/46* (2013.01)

(58) Field of Classification Search
CPC ............... G01R 33/46; G01R 33/5676; G01R 33/56572; G01N 24/08
See application file for complete search history.

(56) References Cited

U.S. PATENT DOCUMENTS

| 2002/0036498 A1 | 3/2002 | Uetake et al. |
| 2004/0051527 A1 | 3/2004 | Mugler, III et al. |
| 2007/0219442 A1 | 9/2007 | Aletras et al. |

FOREIGN PATENT DOCUMENTS

| EP | 1139114 A2 | 10/2001 |
| JP | 2001292976 A | 10/2001 |

(Continued)

OTHER PUBLICATIONS

Gold, G. E., et al.; Driven Equilibrium Magnetic Resonance Imaging of Articular Cartilage: Initial Clinical Experience; 2005; J. MRI; 21(4)476-481.

(Continued)

*Primary Examiner* — Dixomara Vargas

(57) ABSTRACT

The invention relates to a method of magnetic resonance (MR) imaging of at least a portion of a body (10) placed in a stationary and substantially homogeneous main magnetic field. The method comprises the following steps; —exciting nuclear magnetization selectively within a spatially restricted volume of interest (20) by subjecting the portion to an imaging sequence (IMG) comprising at least one RF pulse (α) and switched magnetic field gradients (GX/GY); —acquiring at least one MR imaging signal from the volume of interest (20); —exciting nuclear magnetization within a spatially restricted navigator volume (21) by subjecting said portion to a navigator sequence (NAV) comprising at least one RF pulse and switched magnetic field gradients, wherein the navigator volume (21) at least partially overlaps with the volume of interest (20); —acquiring at least one MR navigator signal from said navigator volume (21); —reconstructing a MR image from the acquired MR imaging signals. It is an object of the invention to enable MR imaging with reliable motion detection and high image quality. For this purpose, the invention proposes that the nuclear magnetization within the volume of interest (20) is transformed back into longitudinal magnetization prior to application of the navigator sequence (NAV) by subjecting said portion to an unlabeling sequence (UNLBL) comprising at least one RF pulse (−α).

16 Claims, 4 Drawing Sheets

(51) Int. Cl.
*G01R 33/567* (2006.01)
*G01R 33/46* (2006.01)

(56) References Cited

FOREIGN PATENT DOCUMENTS

| | | |
|---|---|---|
| JP | 2002165774 A | 6/2002 |
| WO | 2007004123 A2 | 1/2007 |
| WO | 2008041060 A1 | 4/2008 |

OTHER PUBLICATIONS

Handa, S., et al.; In Vivo Assessment of the Trabecular Bone Microstructure of the Distal Radius Using a Compact MRI System; 2009; Magn. Reson. Med. Sci.; 8(1)39-42.

Hargreaves, B. A., et al.; MR Imaging of Articular Cartilage Using Driven Equilibrium; 1999; MRM; 42:695-703.

Song, H. K., et al.; In Vivo Micro-Imaging Using Alternating Navigator Echoes with Applications to Cancellous Bone Structural Analysis; 1999; MRM; 41:947-953.

Wehrli, F. W., et al.; Role of Magnetic Resonance for Assessing Structure and Function of Trabecular Bone; 2002; Topics in Magnetics Resonance Imaging; 13(5)335-356.

MR IMAGING USING NAVIGATORS

FIELD OF THE INVENTION

The present invention relates to the field of magnetic resonance (MR). It finds particular application in conjunction with MR imaging methods and MR devices for diagnostic purposes, and will be described with particular reference thereto. However, it is to be appreciated that the present invention is also amenable to other like applications such as MR spectroscopy.

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field extends perpendicular to the z-axis (also referred to as longitudinal axis), so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant T1 (spin lattice or longitudinal relaxation time), and the magnetization in the direction perpendicular to the z direction relaxes with a second time constant T2 (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image by means of Fourier transformation.

BACKGROUND OF THE INVENTION

In a variety of MRI applications, motion of the examined object (the patient) can adversely affect image quality. Acquisition of sufficient MR signals for reconstruction of an image takes a finite period of time. Motion of the object to be imaged during that finite acquisition time typically results in motion artifacts in the reconstructed MR image. In conventional MR imaging approaches, the acquisition time can be reduced to a very small extent only, when a given resolution of the MR image is specified. In the case of medical MR imaging, motion artifacts can result for example from cardiac cycling, respiratory cycling, and other physiological processes, as well as from patient motion. In dynamic MR imaging scans, the motion of the examined object during data acquisition leads to different kinds of blurring, misregistration, deformation and ghosting artifacts.

Prospective motion correction techniques such as the so-called navigator technique have been developed to overcome problems with respect to motion by prospectively adjusting the imaging parameters, which define the location and orientation of the volume of interest within the imaging volume. In the navigator technique hereby, a set of MR navigator signals is acquired from a spatially restricted volume (navigator beam) that crosses the diaphragm of the examined patient. For registering the MR navigator signals, so-called 2D RF pulses may be used. These excite the spatially restricted navigator volume, for example of pencil beam shape, which is read out using a gradient echo. Other ways to detect the motion-induced momentary position of the volume of interest is the acquisition of two-dimensional sagittal slices that are positioned at the top of the diaphragm, or the acquisition of three-dimensional low-resolution data sets. The respective navigator volume is interactively placed in such a way that a displacement value indicating the instantaneous position of the diaphragm can be reconstructed from the acquired MR navigator signals and used for motion correction of the volume of interest in real time. The navigator technique is primarily used for minimizing the effects of breathing motion in body and cardiac exams where respiratory motion can severely deteriorate the image quality. Gating and image correction based on the MR navigator signals was introduced to reduce these artifacts.

The afore-described navigator technique can generally be applied in different fields of MR imaging in order to detect a specific change in imaging conditions. A further example is the triggering of an imaging sequence after the bolus arrival of a contrast agent at a specific organ of interest.

Subsequent to the measurement of the MR navigator signals, usually a series of phase-encoded spin echoes is generated by an appropriate imaging sequence of RF pulses and magnetic field gradient pulses. These spin echoes are measured as MR imaging signals for reconstructing an MR image therefrom, for example by 2D Fourier transformation.

As mentioned before, the restricted navigator volume is ideally placed over the interface (localized at the dome of the right hemidiaphragm) between the liver and the lung in order to detect the breathing state of the examined patient. This is because of the high MR signal contrast between the lung and the liver. Particularly in abdominal applications, the problem arises that the volume of interest, from which the MR imaging signals are acquired, partially overlaps with the navigator volume. Usually, the acquisition of the MR imaging signals is interleaved with the acquisition of the MR navigator signals without temporal delay. As a consequence, the nuclear magnetization within the volume of interest remains saturated after measuring the MR imaging signals. The resulting saturation bands in the MR navigator signals lead to a wrong detection of the contrast edge indicating the position of the diaphragm. For this reason, the known navigator methods are difficult to apply for MR imaging of the liver or the kidneys. It can not be avoided that the navigator volume is (at least partly) superimposed upon the respective volumes of interest, with the negative consequence that the image quality is considerably degraded due to the incorrect detection of the respiratory motion state WO 2008/041060 A1 addresses the problem that the nuclear magnetization within the restricted navigator volume remains saturated after measuring the MR navigator signals. In this case, the remaining saturation has the negative consequence that the navigator volume appears as a saturated region in the reconstructed MR images. It is proposed in the cited document to apply a navigator unlabeling sequence prior to generating the actual imaging or spectroscopic sequence. The effect of the navigator unlabeling sequence is that the nuclear magnetization within the restricted navigator volume is converted back into longitudinal magnetization. In this way, the acquisition of MR imaging signals starts without disturbance by the navigator. However, the problem remains that the nuclear magnetization within the volume, from which the MR imaging signals are acquired, remains saturated when the imaging sequence and the navigator sequence are repeatedly applied in an interleaved fashion. The cited document does not propose a solution for the above-mentioned problems associated with incorrect motion detection due to saturation bands in the MR navigator signals.

SUMMARY OF THE INVENTION

From the foregoing it is readily appreciated that there is a need for an improved MR imaging method. It is consequently an object of the invention to enable MR imaging with reliable motion detection and high image quality.

In accordance with the invention, a method of MR imaging of at least a portion of a body of a patient placed in a stationary and substantially homogeneous main magnetic field is disclosed. The method comprises the following steps:
a) exciting nuclear magnetization selectively within a spatially restricted volume of interest by subjecting the portion to an imaging sequence comprising at least one RF pulse and switched magnetic field gradients;
b) acquiring at least one MR imaging signal from the volume of interest;
c) transforming the nuclear magnetization within the volume of interest back into longitudinal magnetization by subjecting said portion to an unlabeling sequence comprising at least one RF pulse;
d) exciting nuclear magnetization within a spatially restricted navigator volume by subjecting said portion to a navigator sequence comprising at least one RF pulse and switched magnetic field gradients, wherein the navigator volume at least partially overlaps with the volume of interest;
e) acquiring at least one MR navigator signal from said navigator volume;
f) reconstructing a MR image from the acquired MR imaging signals.

The gist of the invention is the application of the unlabeling sequence prior to the acquisition of the MR navigator signals in an interleaved acquisition scheme of MR imaging signals and navigator signals. The effect of the unlabeling sequence is that the nuclear magnetization within the volume of interest, from which the MR imaging signals are acquired, is converted back into longitudinal magnetization. In this way, the effect of the preceding imaging sequence is largely neutralized and the actual navigator acquisition starts without disturbance by saturation bands and, consequently, without the risk of incorrect motion correction. Since there remains essentially no saturated magnetization within the volume of interest before the next navigator acquisition starts, imaging and/or spectroscopy can be performed without restrictions with regard to the location of the volume of interest. High quality MR imaging and/or spectroscopy are possible even if the navigator volume and the volume of interest are fully or partially overlapping, such as in abdominal applications.

It has to be noted that the above-mentioned 2D RF pulses may be used for acquiring the MR navigator signals according to the invention. The acquisition of two-dimensional sagittal slices that are positioned at the top of the diaphragm, or the acquisition of three-dimensional low-resolution data sets as navigator signals is also feasible. An alternative method for generating MR navigator signals in a spatially restricted navigator volume is to excite nuclear magnetization by means of subsequent slice-selective RF pulses. The slices acted upon by the RF pulses are selected such that they are crossing each other along the desired beam-shaped volume. The MR navigator signal may then easily be detected as a spin echo in the presence of a read out gradient along the direction of the line of intersection of the slices. Motion of the examined portion of the body along this direction can be monitored in this way.

According to one aspect of the invention, the imaging acquisiton includes several image acquisistion sequences, e.g. to acquire magnetic resonance signals for several k-space profiles or from several volumes of interest, such as different slices. In this aspect of the invention magnetic resonance signals from several slices are acquired per navigator, then the unlabeling phase is sufficient for the slice acquired prior to the navigator. Notably, previous slices then already have experienced a delay and remaining transverse magnetisation is very small.

According to a preferred embodiment of the invention, at least one displacement value indicating motion of the body is derived from the at least one MR navigator signal, wherein the position of the volume of interest is adjusted on the basis of the at least one displacement value during several repetitions of at least steps a) through e). In this embodiment, prospective motion correction is applied to overcome problems with respect to motion by prospectively adjusting the imaging parameters, which define the location and orientation of the volume of interest within the imaging volume. The navigator technique of the invention may be applied, for example, for minimizing the effects of breathing motion of the patient, which can severely deteriorate the image quality. Alternatively, gating of the acquisition of the MR imaging signals based on the MR navigator signals can be applied to reduce these artifacts.

According to a further preferred embodiment of the invention, the examined body is subsequently subjected to the imaging sequence, the unlabeling sequence, and the navigator sequence with a negligible temporal delay. Since saturation bands are significantly reduced in the MR navigator signals after application of the unlabeling sequence, the imaging sequence and the subsequent navigator sequence can be applied in rapid succession without having to wait for relaxation of the nuclear magnetization within the volume of interest. The overall scan time can be significantly reduced in this way. Against this background, the meaning of the expression 'without temporal delay' includes all delay values being significantly shorter than the relevant relaxation times $T_1$ or $T_2$.

As mentioned above, it is to be appreciated that the present invention is also applicable for MR spectroscopy. In this respect, a method of MR spectroscopy is disclosed, the method comprising the following steps:
a) exciting nuclear magnetization selectively within a spatially restricted volume of interest within an object by subjecting the object to a spectroscopy sequence comprising at least one RF pulse and switched magnetic field gradients;
b) acquiring at least one MR spectroscopy signal from the volume of interest;
c) transforming the nuclear magnetization within the volume of interest back into longitudinal magnetization by subjecting said portion to an unlabeling sequence comprising at least one RF pulse;
d) exciting nuclear magnetization within a spatially restricted navigator volume by subjecting said portion to a navigator sequence comprising at least one RF pulse and switched magnetic field gradients, wherein the navigator volume at least partially overlaps with the volume of interest;
e) acquiring at least one MR navigator signal from said navigator volume;
f) deriving a MR spectrum from the acquired MR spectroscopy signals.

The MR imaging or spectroscopy methods of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing a MR image from the MR signals. The method of the invention may be implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF EMBODIMENTS

Figure 1:
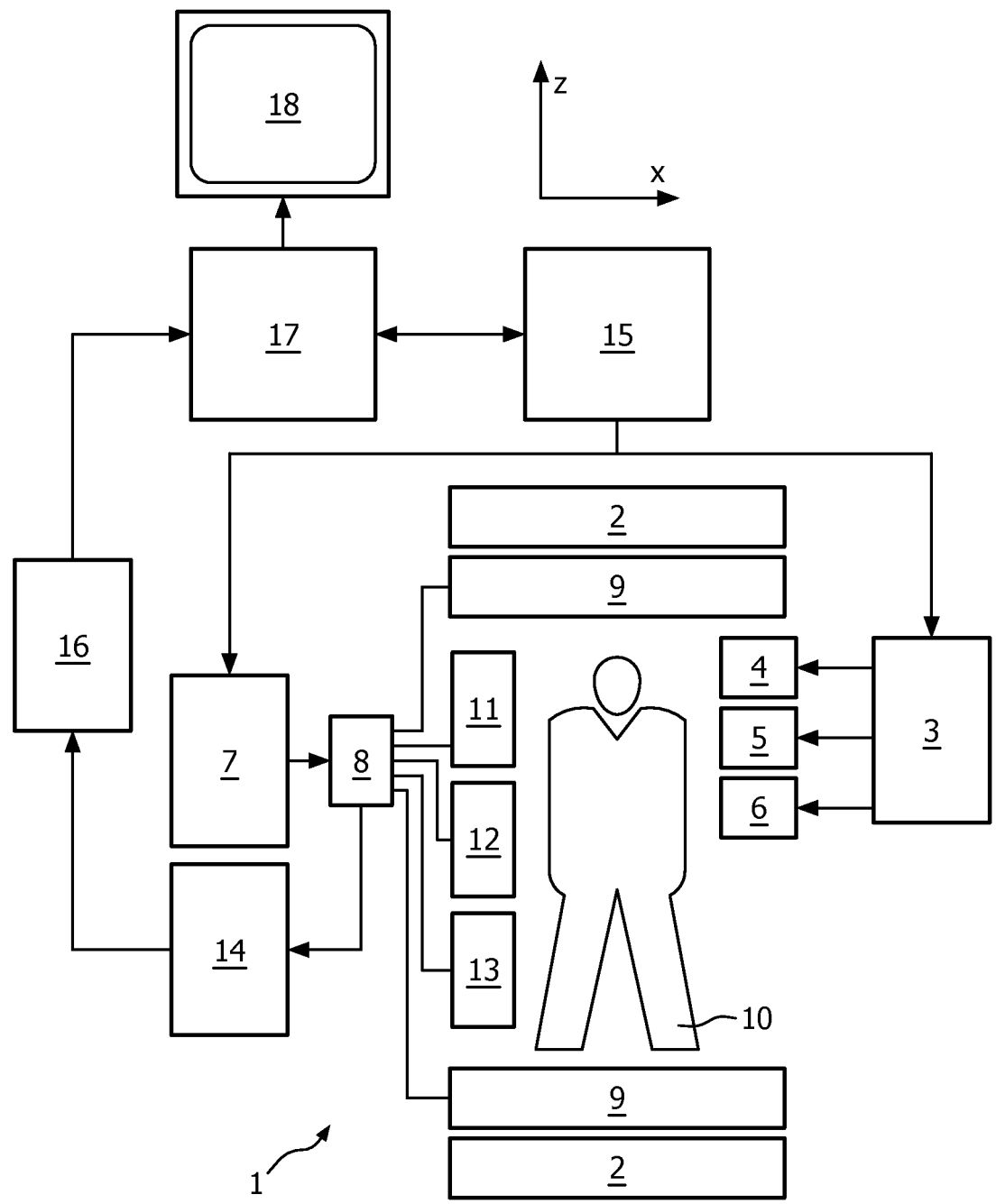
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A RF frequency transmitter 7 transmits RF pulses or pulse packets, via a send-/receive switch 8, to a whole-body volume RF coil 9 to transmit RF pulses into the examination volume. A typical imaging sequence or navigator sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the whole body volume RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

The host computer 15 and the reconstruction processor 17 comprise a programming by which they are enabled to execute the above-described MR imaging method of the invention.

Figure 2:
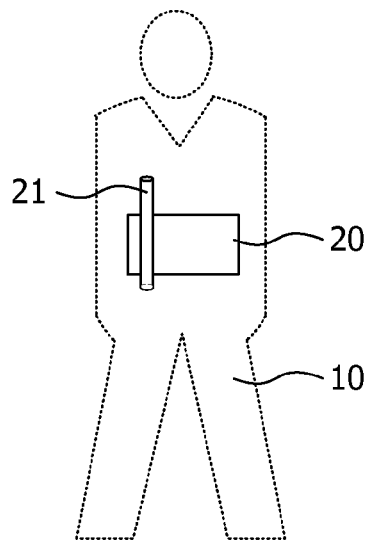
FIG. 2 schematically shows the positions of the volume of interest and the navigator volume within the body of the patient.

FIG. 2 shows the positions of a spatially restricted volume of interest 20 and a navigator volume 21 within the body 10 according to the invention. The per se known navigator technique enables the excitation of nuclear magnetization and the acquisition of corresponding MR navigator signals within the spatially restricted pencil beam shaped navigator volume 21. FIG. 2 illustrates an abdominal application, in which MR imaging signals are acquired from volume of interest 20 including, for example, the liver, the kidneys, or the renal arteries. To detect the breathing state of the patient, the high difference of the amplitude of the MR signal between the lung and the diaphragm suggests ideally placing the navigator volume 21 over the diaphragm/lung interface. In the depicted abdominal application, the volume of interest 20 overlaps with the navigator volume 21.

Figure 3A:
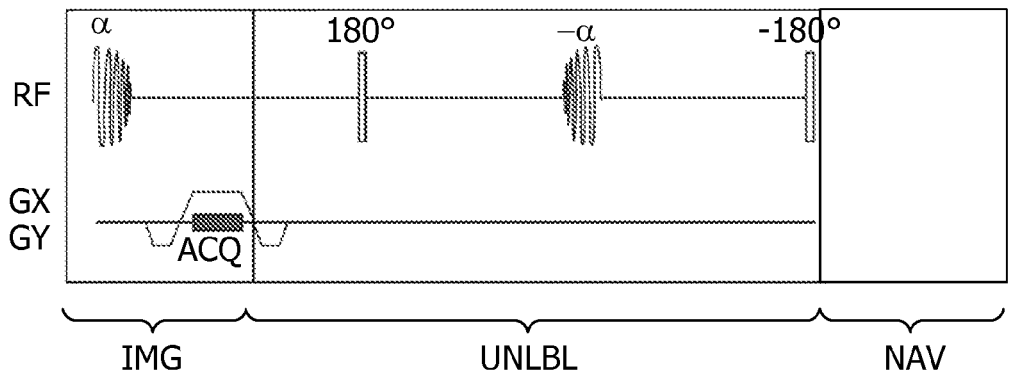
FIG. 3(a, b) shows diagrams illustrating embodiments of unlabeling sequences in accordance with the invention.

A first sequence design in accordance with the method of the present invention is schematically depicted in FIG. 3*a*. The diagram shows the temporal succession of radio frequency pulses RF and of magnetic field gradient pulses GX, GY. A patient placed in a stationary and substantially homogeneous main magnetic field (as shown in FIG. 1) is subjected to these pulses during the MR imaging procedure of the invention.

The sequence begins with an imaging sequence IMG, which is a gradient echo sequence in the depicted embodiment. The imaging sequence IMG comprises a spatially selective RF pulse α, by which nuclear magnetization is excited within the volume of interest 20. MR imaging signals generated by the RF pulse α and switched magnetic field gradients GX/GY are acquired during an acquisition period ACQ. These MR imaging signals are measured and used for reconstruction of a diagnostic MR image, for example of the kidneys or the renal arteries of the patient.

After the imaging sequence IMG, an unlabeling sequence UNLBL is applied without a temporal delay. The unlabeling sequence comprises, at its beginning, a switched magnetic field gradient GX/GY for rephasing of the nuclear magnetization. Thereafter, an inverse spatially selective RF pulse –α is applied, which transforms the nuclear magnetization within the volume of interest 20 back into longitudinal magnetization. Moreover, spatially non-selective 180° RF pulses are applied to overcome effects due to inhomogeneities of the main magnetic field.

The unlabeling sequence UNLBL is followed, again without a temporal delay, by navigator sequence NAV as it is known per se in the art. Details of the navigator sequence NAV are not depicted in FIG. 3*a*. The navigator sequence NAV may comprise a 2D pulse consisting of a shaped RF pulse, during which magnetic field gradients GX/GY are switched rapidly. Nuclear magnetization within the restricted two-dimensional pencil beam shaped navigator volume 21 is excited at the dome of the right diaphragm of the patient by these pulses. During the application of the navigator sequence NAV, a MR navigator signal is measured in the presence of a read-out gradient in the direction of the longitudinal axis of the navigator volume 21, thereby enabling the reconstruction of an one-dimensional image of the navigator volume. This image is used to monitor the position of the patient's diaphragm during respiration.

After measuring the MR navigator signal, a further interleaved succession of the depicted imaging sequence IMG, unlabeling sequence UNLBL, and navigator sequence NAV is applied, for example for the purpose of generating a dynamic series of MR images. Because of the presence of the unlabeling sequence UNLBL, there remains essentially no saturated nuclear magnetization within the volume of interest 20 before the next navigator sequence NAV starts. Hence, reduced saturation bands occur in the acquired MR navigator signals, misdetection of the position of the diaphragm can be prevented, and the instantaneous respiratory motion state can be derived reliably. In order to further improve the reliabilty of the detection of the position of the diaphragm, the knowledge of the previously applied volume selections may be taken into account. The corresponding displacement values can be used to prospectively adjust the imaging parameters, which define the location and orientation of the volume of interest of the subsequent imaging sequence IMG. A series of high-quality MR images can be obtained in this way. The unlabeling sequence UNLBL causes a minor extension of the total scan time by 10 to 20 ms in typical cases.

Figure 3B:
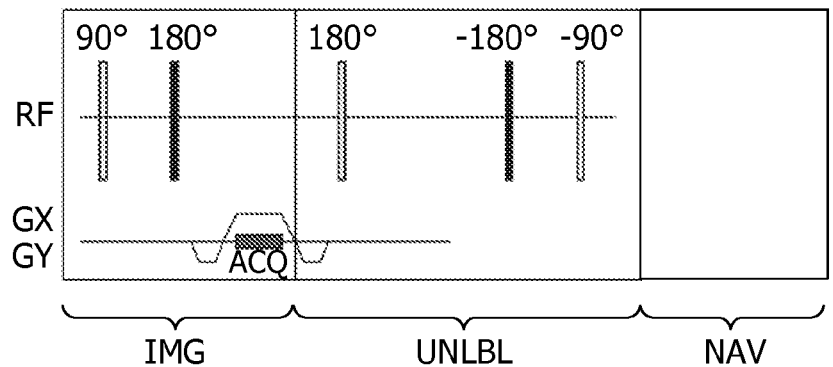

A further sequence design in accordance with the method of the present invention is illustrated in FIG. 3*b*. In this embodiment, the imaging sequence IMG is a spin echo sequence, in which the MR imaging signals are generated by means of a spatially selective 90° RF pulse followed by a 180° RF pulse. For recovering the magnetization within the volume of interest 21, the unlabeling sequence comprises corresponding inverse RF pulses of –180° and –90°. For overcoming effects due to inhomogeneities of the main magnetic field, a spatially selective 180° RF pulse may be applied additionaly, as depicted in FIG. 3*b*, during the unlabeling sequence UNLBL.

Figure 4A:
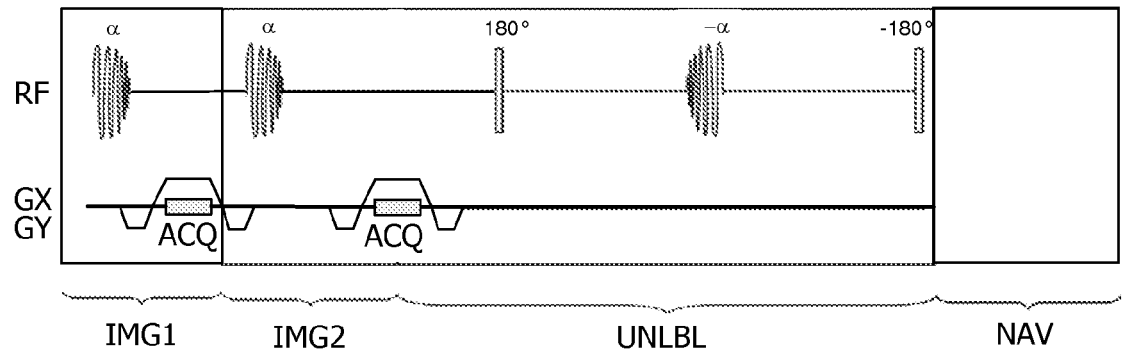
FIG. 4(a, b, c) shows diagrams illustrating more embodiments of unlabeling sequences in accordance with the invention.

FIG. 4(*a, b,c*) shows diagrams illustrating more embodiments of unlabeling sequences in accordance with the invention. The diagram shows the temporal succession of radio frequency pulses RF and of magnetic field gradient pulses GX, GY. A patient placed in a stationary and substantially homogeneous main magnetic field (as shown in FIG. 1) is subjected to these pulses during the MR imaging procedure of the invention.

The sequence begins with a first imaging sequence IMG1, followed by a second imaging sequnece IMG2, which are gradient echo sequences in the depicted embodiment. The imaging sequences IMG1, IMG2 comprises a spatially selective RF pulse α, by which nuclear magnetization is excited within the volumes of interest 20. MR imaging signals generated by the RF pulse α and switched magnetic field gradients GX/GY are acquired during an acquisition period ACQ. These MR imaging signals are measured and used for reconstruction of a diagnostic MR image, for example of the kidneys or the renal arteries of the patient.

After the imaging sequences IMG1 and IMG2, an unlabeling sequence UNLBL is applied without a temporal delay. The unlabeling sequence comprises, at its beginning, a switched magnetic field gradient GX/GY for rephasing of the nuclear magnetization. Thereafter, an inverse spatially selective RF pulse –α is applied, which transforms the nuclear magnetization within the volume of interest 20 back into longitudinal magnetization. Moreover, spatially non-selective 180° RF pulses are applied to overcome effects due to inhomogeneities of the main magnetic field.

The unlabeling sequences UNLBL is followed, again without a temporal delay, by navigator sequence NAV as it is known per se in the art. Details of the navigator sequence NAV are not depicted in FIG. 3*a*. The navigator sequence NAV may comprise a 2D pulse consisting of a shaped RF pulse, during which magnetic field gradients GX/GY are switched rapidly. Nuclear magnetization within the restricted two-dimensional pencil beam shaped navigator volume 21 is excited at the dome of the right diaphragm of the patient by these pulses. During the application of the navigator sequence NAV, a MR navigator signal is measured in the presence of a read-out gradient in the direction of the longitudinal axis of the navigator volume 21, thereby enabling the reconstruction of an one-dimensional image of the navigator volume. This image is used to monitor the position of the patient's diaphragm during respiration.

After measuring the MR navigator signal, a further interleaved succession of the depicted imaging sequences IMG1, IMG2 etc, unlabeling sequence UNLBL, and navigator sequence NAV is applied, for example for the purpose of generating a dynamic series of MR images. Because of the presence of the unlabeling sequence UNLBL, there remains essentially no saturated nuclear magnetization within the volume of interest 20 before the next navigator sequence NAV starts. Hence, reduced saturation bands occur in the acquired MR navigator signals, misdetection of the position of the diaphragm can be prevented, and the instantaneous respiratory motion state can be derived reliably. In order to further improve the reliabilty of the detection of the position of the diaphragm, the knowledge of the previously applied volume selections may be taken into account. The corresponding displacement values can be used to prospectively adjust the imaging parameters, which define the location and orientation of the volume of interest of the subsequent imaging sequence IMG. A series of high-quality MR images can be obtained in this way. The unlabeling sequence UNLBL causes a minor extension of the total scan time by 10 to 20 ms in typical cases.

Figure 4B:
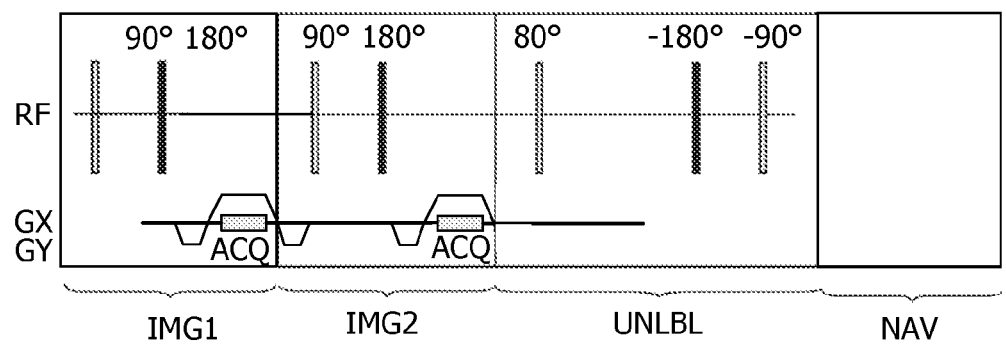
Figure 4C:
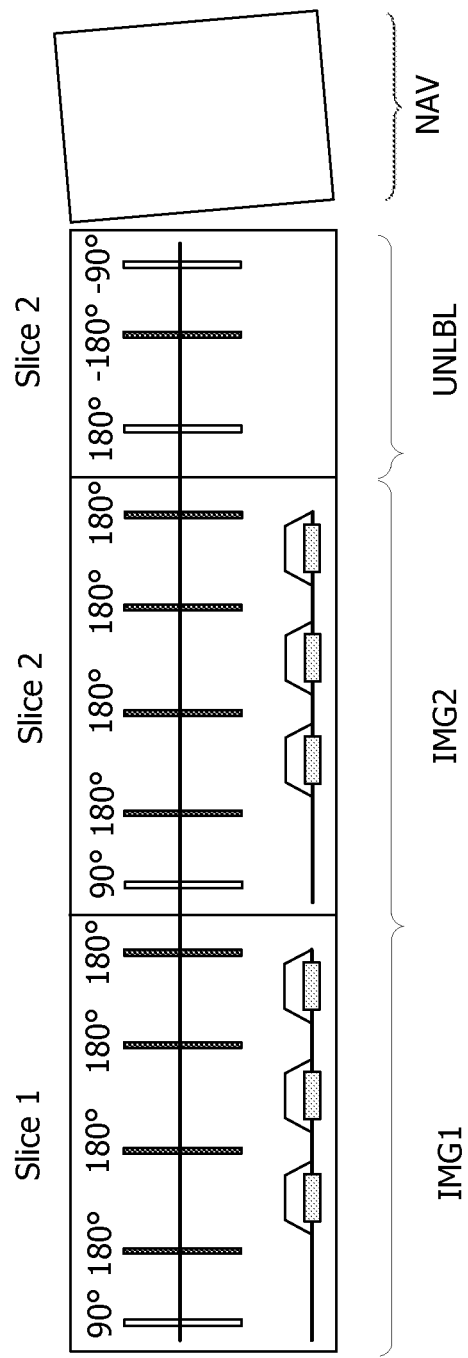

A further sequence design in accordance with the method of the present invention is illustrated in FIG. 4b. In this embodiment, the imaging sequences IMG1, IMG2 are a spin echo sequences, in which the MR imaging signals are generated by means of a spatially selective 90° RF pulse followed by a 180° RF pulse. For recovering the magnetization within the volume of interest 21, the unlabeling sequence comprises corresponding inverse RF pulses of −180° and −90°. For overcoming effects due to inhomogeneities of the main magnetic field, a spatially selective 180° RF pulse may be applied additionaly, as depicted in FIG. 3b, during the unlabeling sequence UNLBL. In FIG. 4c an example is shown in which the imaging sequences IMG1 and IMG2 are turbo spin echo sequences and the unlabeling sequence UMLBL employs an inverse −180° pulse and a −90° pulse. Further a selective 180° is used to compensate for $B_0$ (main field) inhomogeneities. This approach in practice leads to an effective reconstruction of the excitetd slice, while misdetection of the diaphragm edge is avoided. In practice only a minor extension of the acquisition time of about 10-20 ms occurs.

The invention claimed is:

1. A method of magnetic resonance (MR) imaging of at least a portion of a body placed in a stationary and substantially homogeneous main magnetic field, the method comprising:
   a) exciting nuclear magnetization selectively within a spatially restricted volume of interest by subjecting the portion to an imaging sequence (IMG) comprising at least one RF pulse ($\alpha$) and switched magnetic field gradients (GX/GY);
   b) acquiring at least one MR imaging signal from the spatially restricted volume of interest;
   c) transforming the nuclear magnetization within the spatially restricted volume of interest back into longitudinal magnetization by subjecting said portion to an unlabeling sequence (UNLBL) comprising at least one RF pulse ($-\alpha$);
   d) exciting nuclear magnetization within a spatially restricted navigator volume by subjecting said portion to a navigator sequence (NAV) comprising at least one RF pulse and switched magnetic field gradients, wherein the navigator volume at least partially overlaps with the spatially restricted volume of interest;
   e) acquiring at least one MR navigator signal from said navigator volume;
   f) reconstructing a MR image from the acquired MR imaging signals.

2. The method according to claim 1 in which several MR imaging signals are acquired from several spatially restricted volumes of interest and the unlabeling sequence transforms the nuclear magnetization within said spatially restricted volumes of interest back into longitudinal magnetization.

3. The method according to claim 1, wherein the MR imaging signals are acquired by a spin echo sequence and the unlabeling sequence includes an inverse 180° RF pulse and a 90° RF pulse.

4. The method according to claim 1, wherein at least one displacement value indicating motion of the body is derived from the at least one MR navigator signal, and wherein the position of the spatially restricted, volume of interest is adjusted on the basis of the at least one displacement value during several repetitions of at least steps a) through e).

5. The method according to claim 1, wherein the portion is subsequently subjected to the imaging sequence (IMG), the unlabeling sequence (UNLBL), and the navigator sequence (NAV) without temporal delay.

6. The method according to claim 1, wherein the navigator sequence (NAV) and/or the unlabeling sequence (UNLBL) comprise at least one shaped RF pulse ($\alpha$, $-\alpha$) and at least one switched magnetic field gradient (GX, GY).

7. The method according to claim 1, wherein the unlabeling sequence comprises at least one spatially selective and non-selective 180° RF pulse.

8. A method of magnetic resonance (MR) spectroscopy, the method comprising:
   a) exciting nuclear magnetization selectively within a spatially restricted volume of interest within an object by subjecting the object to a spectroscopy sequence comprising at least one RF pulse and switched magnetic field gradients;
   b) acquiring at least one MR spectroscopy signal from the spatially restricted volume of interest;
   c) transforming the nuclear magnetization within the spatially restricted volume of interest back into longitudinal magnetization by subjecting said portion to an unlabeling sequence comprising at least one RF pulse;
   d) exciting nuclear magnetization within a spatially restricted navigator volume by subjecting said portion to a navigator sequence comprising at least one RF pulse and switched magnetic field gradients, wherein the navigator volume at least partially overlaps with the spatially restricted volume of interest;
   e) acquiring at least one MR navigator signal from said navigator volume;
   f) providing deriving a MR spectrum from the acquired MR spectroscopy signals.

9. A magnetic resonance (MR) imaging device comprising:
   a main magnet coil for generating a uniform, steady magnetic field within an examination volume,
   a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing a MR image from the MR signals, wherein the device is configured to:

a) excite nuclear magnetization selectively within a spatially restricted volume of interest by subjecting the portion to an imaging sequence (IMG) comprising at least one RF pulse (α) and switched magnetic field gradients (GX/GY);

b) acquire at least one MR imaging signal from the spatially restricted volume of interest;

c) transform the nuclear magnetization within the spatially restricted volume of interest back into longitudinal magnetization by subjecting said portion to an unlabeling sequence (UNLBL) comprising at least one RF pulse (−α);

d) excite nuclear magnetization within a spatially restricted navigator volume by subjecting said portion to a navigator sequence (NAV) comprising at least one RF pulse and switched magnetic field gradients, wherein the navigator volume at least partially overlaps with the volume of interest;

e) acquire at least one MR navigator signal from said navigator volume; and f) reconstruct a MR image from the acquired MR imaging signals.

10. The MR imaging device according to claim 9, wherein several MR imaging signals are acquired from several spatially restricted volumes of interest and the unlableing sequence transforms the nuclear magnetization within said spatially restricted volumes of interest back into longitudinal magnetization.

11. The MR imaging device according to claim 9, wherein the MR imaging signals are acquired by a spin echo sequence and the unlabeling sequence includes an inverse 180° RF pulse and a 90° RF pulse.

12. The MR imaging device according to claim 9, wherein at least one displacement value indicating motion of the body is derived from the at least one MR navigator signal, and wherein the position of the spatially restricted volume of interest is adjusted on the basis of the at least one displacement value during several repetitions of at a) through e).

13. The MR imaging device according to claim 9, wherein the portion is subsequently subjected to the imaging sequence (IMG), the unlabeling sequence (UNLBL), and the navigator sequence (NAV) without temporal delay.

14. The MR imaging device according to claim 9, wherein the navigator sequence (NAV) and/or the unlabeling sequence (UNLBL) comprise at least one shaped RF pulse (α, −α) and/or at least one switched magnetic field gradient (GX, GY).

15. The MR imaging device according to claim 9, wherein the unlabeling sequence comprises at least one spatially selective or non-selective 180° RF pulse.

16. A non-transitory computer readable medium storing computer program to be run on a magnetic resonance (MR) device, which computer program comprises instructions for:

a) generating an imaging sequence (IMG) comprising at least one RF pulse (α) and switched magnetic field gradients (GX/GY);

b) acquiring at least one MR imaging signal from a spatially restricted volume of interest;

c) transforming the nuclear magnetization within the spatially restricted volume of interest back into longitudinal magnetization by generating an unlabeling sequence (UNLBL) comprising at least one RF pulse (−α);

d) generating a navigator sequence (NAV) comprising at least one RF pulse and switched magnetic field gradients;

e) acquiring at least one MR navigator signal from a spatially restricted navigator volume, wherein the navigator volume at least partially overlaps with the spatially restricted volume of interest;

f) reconstructing a MR image from the acquired MR imaging signals.

* * * * *